United States Patent [19]

Carter et al.

[11] Patent Number: 5,736,408
[45] Date of Patent: Apr. 7, 1998

[54] METHOD FOR THE DETECTION OF UROBILINOGEN IN URINE ON AN AUTOMATED ANALYZER

[76] Inventors: Jesse M. Carter, 910 S. Rome Ave., Tampa, Fla. 33606; Jack V. Smith, 8505 42nd Ave. N., St. Petersburg, Fla. 33709

[21] Appl. No.: 599,988

[22] Filed: Feb. 14, 1996

Related U.S. Application Data

[63] Continuation-in-part of Ser. No. 347,122, Nov. 23, 1994, abandoned.

[51] Int. Cl.⁶ .................................................. G01N 33/00
[52] U.S. Cl. ............................ 436/97; 436/43; 436/63; 436/164; 436/175; 436/176
[58] Field of Search ............................ 436/12, 43, 63, 436/97, 164, 171, 175, 176; 422/63, 67, 68.1, 82.05, 82.09

[56] References Cited

U.S. PATENT DOCUMENTS

| | | | |
|---|---|---|---|
| 3,630,680 | 12/1971 | Rittersdorf et al. | 436/97 |
| 3,814,586 | 6/1974 | Fraser, Jr. et al. | 436/97 |
| 3,850,576 | 11/1974 | Rittersdorf et al. | 436/97 |
| 3,853,466 | 12/1974 | Rittersdorf et al. | 436/97 |
| 3,989,462 | 11/1976 | Hirsch | 436/97 |
| 4,290,771 | 9/1981 | Hirsch | 436/97 |
| 4,665,038 | 5/1987 | Sakata et al. | 436/97 |
| 4,703,013 | 10/1987 | Louderback et al. | 436/12 |
| 5,149,272 | 9/1992 | Wu et al. | 436/97 |

*Primary Examiner*—Maureen M. Wallenhorst

[57] ABSTRACT

Method of detecting urobilinogen in urine using a chemical detection means with an indicator that will produce a detectable quantitative response in the presence of, or lack of urobilinogen in urine on an automated analyzer.

6 Claims, No Drawings

5,736,408

METHOD FOR THE DETECTION OF UROBILINOGEN IN URINE ON AN AUTOMATED ANALYZER

PRIOR APPLICATIONS

This application is a continuation-in-part of application Ser. No. 08/347,122, filed Nov. 23, 1994 now abandoned.

BACKGROUND OF THE INVENTION

The present invention is concerned with an improved diagnostic agent for the rapid and sensitive detection of urobilinogen in body fluids, particularly in urine.

The detection of urobilinogen is of great importance in the diagnosis of disease of the liver. Urobilinogen is a bile pigment that results from the degradation of hemoglobin, it is produced in the intestine from the reduction of bilirubin by the intestinal bacteria. Approximately half of the urobilinogen is reabsorbed from the intestine into the blood, recirculates to the liver, and is secreted back into the intestine through the bile duct. The urobilinogen remaining in the intestine is excreted in the feces, where it is oxidized to urobilin, the pigment responsible for the characteristic brown color of the feces. Urobilinogen appears in the urine because, as it circulates in the blood en-route to the liver, it may pass through the kidney and be filtered out of the blood by the glomerulus. Therefore, a small amount of urobilinogen (less than 1 mg/dl) is normally in the urine.

Increased urine urobilinogen is seen in liver disease and hemolytic disorders. Impairment of liver function decreases the liver's ability to process the urobilinogens recirculated from the intestine, and the excess urobilinogen remaining in the blood is filtered by the kidney. Measurement of urine urobilinogen can be a valuable indicator in the detection of early liver disease.

Although it cannot be determined by reagent strips (i.e. test papers/dipsticks), the absence of urobilinogen in the urine and feces is also diagnostically significant, because this represents obstruction of the bile duct and prevents the normal passage of bilirubin into the intestine.[1]

It is known that urobilinogen bodies (bilance), indole, sulfonamides, prophobilinogens, urine indican and 5-hydroxy-indoleacetic can be detected with a solution of p-dimethyl-aminobenzaldehyde, in hydrocloric acid. This detection reaction is known in the literature as Ehrlich's reaction; it has achieved considerable importance, especially in medical diagnosis, for the detection of "increased urobilinogens" in urine. Although the test is not specific, it is regarded as being indicative of liver and gall bladder function.

SUMMARY OF THE INVENTION

Test papers (dipsticks, strips) used in the chemical determination of urobilinogen are based on Ehrlich's reaction and the diazonium coupling reaction (U.S. Pat. No. 3,853,466) for clinical diagnostic purposes. In fact, Rittersdorf, et al. (U.S. Pat. Nos. 3,630,680 and 3,850,576), Sakata et al.(U.S. Pat. No. 4,665,038), Hirsh (U.S. Pat. Nos. 4,290,771 and 3,989,462) and Fraser, Jr. et al.(U.S. Pat. No. 3,814,586) all teach methods for using the diazo reagents on test strips and visually observing color reaction. The above annotated list of assay devices utilizing prior art includes dipsticks, or impregnated test strips for the analysis of urinary constituents. None of the prior devices foresee or teach a multiple or single liquid reagent system designed specifically for autoanalyzers to quantitate urinary constituents.

Test papers using these methods suffer from many important disadvantages viz., (1) the color reaction develops so slowly that it is necessary to wait for at least one minute before reading results; (2) the test papers naturally possess the non-specificity of Ehrlich's test and thus false positive results cannot be excluded; (3) the diazonium method reacts with nitrite, a urinary constituent often found in the urine of patients with gram negative bacterial infections, 3; (4) the diazonium method suffers from interference by many common medicines including phenazopyridine (an analgesic for urinary tract infection) a medication that causes false positives; (5) and perhaps the most significantly, test papers are not able to determine the total absence of urobilinogen. This latter inadequacy of the prior art has dire diagnostic consequences.[2]

Evidence has indicated that urobilinogen may couple with diazotized sulfanilic to give a yellow colored material. This reaction was discovered by Ehrlich in 1884 and is referred to as the so-called "yellow diazo reaction." Subsequently, the reaction was investigated several times but hitherto it has not been possible to ascertain whether it is, without doubt, a diazo coupling with urobilinogen or whether other materials may also be responsible for the formation of the yellow colored material (see "Biologic der Gallenfarbstoffe," published by George Thieme-Verlag, Stuttgart, Germany, 1960:pp. 32 and 211). Since this is more of a curiosity than a useful agent for clinical-chemical diagnosis, the yellow diazo reaction is practically without importance and is scarcely mentioned in any of the standard reference books.

In U.S. Pat. No. 5,149,272, Wu et. al. (herein after called Wu) teaches a method for detecting bilirubin in blood, serum, and bile on an autoanalyzer. Wu's formulations specifically require a diazotized sulfanilamide, iodide, and a betaine, and therefore does not resemble this new and novel invention which does not contain any of these constituents. It is important to note that Wu's art works on bilirubin in a blood-based sample matrix. Conversely, the proposed new invention is designed for use with a urine-based sample matrix. Wu's invention does not cross react to a significant degree with urobilinogen (i.e. high concentrations of urobilinogen will not yield a positive result for bilirubin). In addition, this new invention will not react with bilirubin to yield a positive result for urobilinogen.

Other patents that teach bilirubin assays include Wahlefeld et. al. (U.S. Pat. No. 3,754,862) and Babb et. al. (U.S. Pat. No. 4,468,467). Wahlefeld's and Babb's art includes primary components not found in this invention including Chlorophenyl diazoniums and alkyl-phenol polyethylene oxide, and sulfanilamide and carbonamide diazonium salts respectively. Again these inventions do not detect urobilinogen effectively. In addition they are not formulated for effective usage with urine-based samples on automated analyzers.

In U.S. Pat. No. 3,853,466, Rittersdorf et. al. (hereafter referred to as Rittersdorf) teaches a method to detect urobilinogen in urine, however, said methods do not compensate for many urinary constituents that present problems to diazo chemistries in this sample matrix (whereas the present invention does through the use of chelators). Also this new art utilizes a basic compound to adjust the alkalinity of the urobilinogen to its most reactive state. This compound can also serve other purposes such as chelation of interfering substances in the sample matrix.

In addition, Rittersdorf's art is specifically designed for use on solid, dry carriers (i.e. papers, films, or other absorbent, dry carriers). In fact Rittersdorf clearly states that precipitates that can be extracted by organic solvents are produced when his formulations are added to urine containing urobilinogen. Furthermore, Rittersdorf's art stresses utilization of organic solvents in all of his examples. The inclusion of such high concentrations of low viscosity solvents would introduce a significant error in the accurate dispensing of such a reagent in an auto analyzer. In addition, it would represent a major hazard to shippers, manufacturers, and end users due to the high flamability of these substances.

Most importantly, Rittersdorf's art at best only determines urobilinogen qualitatively, due to the inability to use standards and controls located on the same strip for the same test sample to define and verify a quantitative determination. In addition Rittersdorf's invention is subject to interference from phenazopyridine (causing false positive results), nitrite, and formalin (the latter two causing false negative results). Nitrite occurs in urine specimens of donors with gram-negative bacteria infections of the urinary tract. Formalin is commonly used as a preservative for urine collections.

REFERENCES:
1. Strasinger, S. K.: Urinalysis and Body Fluids. F. A. Davis, Philadelphia, 1994.
2. Tietz, N. W.: Fundamentals of Clinical Chemistry, W. B. Saunders, Philadelpia, 1976.

CITED PATENTS:
1. U.S. Pat. No. 3,853,466
2. U.S. Pat. No. 3,630,680
3. U.S. Pat. No. 3,850,576
4. U.S. Pat. No. 4,665,038
5. U.S. Pat. No. 4,290,771
6. U.S. Pat. No. 3,989,462
7. U.S. Pat. No. 3,814,586
8. U.S. Pat. No. 5,149,272
9. U.S. Pat. No. 3,754,862
10. U.S. Pat. No. 4,468,467

DESCRIPTION OF THE INVENTION

We have now, surprisingly, found that by the use of interference removing compounds and stabilizers in an aqueous, carrier-free, medium (all prior art is carrier dependent) that a sensitive and quantitative method for detecting the presence, or absence of urobilinogen in urine on an autoanalyzer is a reality.

The automated urinalysis assay of this invention offers a method for reducing the consumable materials and labor costs. The assay also offers increased accuracy, sensitivity, and objective quantifiable determinations of urinary constituents for better diagnostic interpretation of the test results of urine, thus enabling a physician to provide better health care for the patient.

This invention satisfies many of the problems unanswered by the prior art: quantitative results, non-subjective results (as would be attained by human visual inspection of Rittersdorf's invention, thereby introducing human error into the result), reproducible results, increased accuracy, precision, sensitivity, carrier-free reagents, reagents designed for autoanalyzer use, reagents uniquely designed for this particular urine analyte overcoming matrix problems previously unanswered by prior art, a method allowing vast improvement of test completion time (hundreds to thousands per hour). The present invention presents a fully automateable walk-away urinalysis assay applicable to any discrete autoanalyzer currently in use, and obviously represents a marked advancement in the art of urinalysis. The clear cut object of the present invention is to provide a more comprehensive method for determining urinary urobilinogen, such method specifically yielding improved health care.

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process, represents a significant improvement over the present art. These improvements which facilitate application to automation and represent significant technical improvement over the previous art include, a buffering system for pH variation in urine by correcting pH to the analytically preferred value prior to analysis and also, stabilizing reaction rates thereby improving linearity and neutralizing the interference effects of the highly complex matrix, of random urines submitted for analysis. Additional technical improvement is due to the addition of components to remove interfering substances yielding reduced assay limitations and increased linearity, accuracy, and precision in the resulting quantitations. These unique reagent formulations allow automation resulting in, but not limited to, enhanced speed, objectivity, accuracy and sensitivity associated with the automated test. A synopsis of the automated testing process follows. The entire automated urinalysis reagent system is loaded into an autoanalyzer. The controls, standards and unknown urine samples are poured into the autoanalyzer sampling cups, individually mixed with each test reagent in discrete cuvettes, the absorbance read and quantitation determined by comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age and physical well being of the patient. All of the factors can interfere with the prior art test procedures.

Thus, it is a primary objective of the present invention to provide techniques for determination of urinary urobilinogen quantitatively and accurately at low medically significant levels.

Thus, the present invention provides a diagnostic agent for the detection of, or lack of urobilinogen in body fluids which comprises a liquid, carrier-free, medium containing at least one indicator capable of yielding a detectable response in the presence of urobilinogen, at least one interference removal compound, stabilizer(s), and surfactant which are all compatible with an automated instrument.

The indicators used in this invention can be aromatic amines formed by diazotization. The diazonium salts are preferably used in the form of the fluoborates (examples: 4-methoxybenzene-diazonium-tetrafluoroborate, 2,4-dimethoxy-benzene diazonium fluoborate, etc.) the stability of which is known; however, other indicators, such as anilines (examples: 4-ethoxyanaline, 4-benzyloxy-anailine, etc.).

Activators can include anionic wetting agents, as well as other compounds. Interference removal compounds can include metal and non-metal chelates.

The urobilinogen method according to the present invention can also contain stabilizing agents for the diazonium salts. Such stabilizers may include for example sodium fluoborate, magnesium sulfate, sodium metaphosphate, arylsulfonates or the like, and salts containing stabilizing anion;

these include, in particular, the sulfate, tetrafluoborate, tetrachlorozincate, hexachloroantimonate, and arylsulfonate ions, as well as other similar compounds.

The present invention also utilizes buffers to remove and/or neutralize ionic and pH interference from urine and inhibit color formation from these interferents.

Wetting agents can also be used to improve fluid flow dynamics, reduce the degassing of reagents, activate color development, and position the inflection point of the color indicator.

Furthermore, the automated liquid reagent system is carrier-free, and independent of the need for filter paper or absorbent carriers (i.e., dipsticks) which all of the prior art cites as essential. Another important aspect of the present invention is that no organic solvent is required for the reagent to work. On the other hand, all of Rittersdorf's examples include the use of methanol as an essential ingredient in quantities of up to 90% in solution. This is a flammable, noxious, and dangerous compound to use. Furthermore, liquids of such low viscosity can not be accurately dispensed in today's auto analyzer (resulting in poor assay precisions), and present a fire and/or explosion hazard. Of further interest it should be noted that use of these solvents would be damage an auto analyzer's sampling and photometric components (tubing and cuvettes) which are often primarily plastic. Also, the present art doesn't require the use of methanol or other solvents one skilled in the art may logically substitute for it such as ethyl acetate, ethanol, or chloroform.

Also, the present invention provides a means for the detection of urobilinogen in urine, which contains at least one indicator in the presence of an acid if required (the presence of acid is indicator dependent). Hydrochloric acid, m-phosphoric acid, oxalic acid, citric acid, potassium bisulfate, and others can be used for this purpose. Metaphosphoric acid is especially useful because of the stability it lends to the indicator diazonium salts.

The automated reagent according to the present invention reacts with urobilinogen-containing urine in about 1 to 30 seconds to form a detectable color developed in the ultraviolet and/or visible range from 340 to 700 nanometers.

The following Examples are given for the purpose of illustrating the present invention:

EXAMPLE I

Liquid reagent is successfully compounded by dissolving the following chemicals at room temperature (25 degree C.):

| Solution I (R1): | |
|---|---|
| 4-methoxybenzene-diazonium-tetrafluroborate | 0.10 g |
| ethylenediaminetetraacetic acid | 0.01 g |
| sodium dodecyl sulfate | 0.10 g |
| oxalic acid | 1.0 g |
| sodium acetate | 10.0 g |
| distilled water add to | 100.0 ml |

Instrument parameters (Hitachi 717):

CHEMISTRY PARAMETERS

| TEST | [URINE UROBIL] |
|---|---|
| ASSAY CODE | [1 POINT]:[0]–[50] |
| SAMPLE VOLUME | [10] |
| R1 VOLUME | [300] [100] [NO] |
| R2 VOLUME | [0] [100] [NO] |
| WAVE LENGTH | [700] [505] |
| CALIB. METHOD | [LINEAR] [0] [0] |
| STD (1) CONC. -POS. | [0]–[1] |
| STD (2) CONC. -POS. | [1.0]–[2] |
| STD (3) CONC. -POS. | [0]–[0] |
| STD (4) CONC. -POS. | [0]–[0] |
| STD (5) CONC. -POS. | [0]–[0] |
| STD (6) CONC. -POS. | [0]–[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0.20]–[1.0] |
| TECH. LIMIT | [0]–[100] |
| INSTRUMENT FACTOR | [1.0] |

For the automated urinalysis of urobilinogen, the single reagent (R1), contains an indicator, 4-methoxybenzene diazonium tetrafluroborate, surfactant/activator, sodium dodecyl sulfate, a chelator to eliminate interfering compounds, ethylenediamine-tetraacetic acid (EDTA sodium salt), an acid to adjust pH of the reaction, oxalic acid, and sodium acetate to help buffer the solution. The reagent is placed in the autoanalyzer. The urine samples, standards, and controls are placed in the autoanalyzer specimen cups. The urine sample, standards and controls are mixed with the single reagent in separate cuvettes. Then the solution is mixed and read at specified intervals as dictated by the instrument parameters and at the specified wavelength (monochromatically) depending on the reagent composition used. In this instance, the assay is read at 505 nanometers and read times are specific to the analyzer. The limit of sensitivity is about 0.00 to 10.00 mg/dl.

EXAMPLE II

Liquid reagents are successfully compounded by dissolving the following chemicals at room temperature (25 degree C.):

| Solution I (R1): | 0.20 g |
|---|---|
| ethylenediaminetetraacetic acid, trisodium | |
| Solution II (R2): | |
| 4-methoxybenzene-diazonium-tetrafluroborate | 0.10 g |
| sodium dodecyl sulfate | 0.15 g |
| meta-phosphoric acid | 1.50 g |
| 2,3 butanedione monoxine | 0.10 g |
| distilled water add to | 100.0 ml |

Instrument parameters (Hitachi 717):

CHEMISTRY PARAMETERS

| TEST | [URINE UROBIL] |
|---|---|
| ASSAY CODE | [1 POINT]:[0]–[50] |
| SAMPLE VOLUME | [10] |
| R1 VOLUME | [125] [100] [NO] |
| R2 VOLUME | [125] [100] [NO] |
| WAVE LENGTH | [700] [545] |
| CALIB. METHOD | [LINEAR] [0] [0] |
| STD (1) CONC. -POS. | [0]–[1] |
| STD (2) CONC. -POS. | [1.0]–[2] |
| STD (3) CONC. -POS. | [0]–[0] |
| STD (4) CONC. -POS. | [0]–[0] |
| STD (5) CONC. -POS. | [0]–[0] |
| STD (6) CONC. -POS. | [0]–[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |

| -continued | |
|---|---|
| PROZONE LIMIT | [0] [UPPER] |
| EXPECTED VALUE | [0.20]-[1.0] |
| TECH. LIMIT | [0]-[100] |
| INSTRUMENT FACTOR | [1.0] |

For the automated urinalysis of urobilinogen, the two part reagent's part one (R1), contains ethylenediaminetetraacetic acid (EDTA sodium salt) to chelate interfering compounds and to activate urobilinogen by adjusting it to an alkaline pH. The second part of the reagent (R2) contains an indicator, 4-methoxybenzene diazonium tetrafluroborate, a surfactant/activator, sodium dodecyl sulfate, 2,3 butanedione monoxine to eliminate interfering compounds such as urea, and an acid to adjust pH of the reaction, metaphosphoric acid. The reagents are placed in the autoanalyzer. The urine samples, standards, and controls are placed in the autoanalyzer specimen cups. The urine samples, standards and controls are mixed with part one of the reagent (R1) in separate cuvettes. Then the second part of the reagent (R2) is added to the solutions in each cuvette, mixed and this reaction mixture is read at specified intervals as dictated by the instrument parameters and at the specified wavelength (monochromatically) depending on the reagent composition used. In this instance, the assay is read at 545 nanometers and read times are specific to the analyzer. The limit of sensitivity is about 0.00 to 10.00 mg/dl.

EXAMPLE III

Liquid reagent is successfully compounded by dissolving the following chemicals at room temperature (25 degree C.):

| Solution I (R1): | |
|---|---|
| para-dimethylaminobenzaldehye | 0.10 g |
| ethylenediaminetetraacetic acid, Fe3+ | 0.01 g |
| sodium dodecyl sulfate | 0.10 g |
| sodium acetate | 10.0 g |
| distilled water add to | 100.0 ml |

Instrument parameters (Hitachi 717):

CHEMISTRY PARAMETERS

| TEST | [URINE UROBIL] |
|---|---|
| ASSAY CODE | [1 POINT]:[0]-[50] |
| SAMPLE VOLUME | [10] |
| R1 VOLUME | [300] [100] [NO] |
| R2 VOLUME | [0] [100] [NO] |
| WAVE LENGTH | [700] [415] |
| CALIB. METHOD | [LINEAR] [0] [0] |
| STD (1) CONC. -POS. | [0]-[1] |
| STD (2) CONC. -POS. | [1.0]-[2] |
| STD (3) CONC. -POS. | [0]-[0] |
| STD (4) CONC. -POS. | [0]-[0] |
| STD (5) CONC. -POS. | [0]-[0] |
| STD (6) CONC. -POS. | [0]-[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0.20]-[1.0] |
| TECH. LIMIT | [0]-[100] |
| INSTRUMENT FACTOR | [1.0] |

Following the compounding of the above formulation (note: the p-dimethlyaminobenzaldehyde is the indicator, and all other constitutients serve the previously indicated functions) urine samples, standards, and controls are placed in the autoanalyzer specimen cups. The urine samples, standards and controls are mixed with part one of the reagent (R1) in separate cuvettes. Then the second part of the reagent (R2) is added to the solutions in each cuvette, mixed and this reaction mixture is read at specified intervals as dictated by the instrument parameters and at the specified wavelength (monochromatically) depending on the reagent composition used. In this instance, the assay is read at 415 nanometers and read times are specific to the analyzer. The limit of sensitivity is about 0.00 to 10.00 mg/dl.

EXAMPLE IV

Liquid reagents are successfully compounded by dissolving the following chemicals at room temperature (25 degree C.):

| Solution I (R1): | |
|---|---|
| sodium dodecyl sulfate | 0.10 g |
| EDTA trisodium salt | 2.0 g |
| distilled water add to | 100.0 ml |
| Solution II (R2): | |
| metaphosphoric acid | 1.50 g |
| lauryl pyridium chloride | 0.10 g |
| 2-methoxy-4-nitrobenzene diazonium tetrafluoroborate | 0.15 g |
| distilled water add to | 100.00 ml |

Instrument parameters (Hitachi 717):

CHEMISTRY PARAMETERS

| TEST | [URINE UROBIL] |
|---|---|
| ASSAY CODE | [1 POINT]:[0]-[50] |
| SAMPLE VOLUME | [10] |
| R1 VOLUME | [125] [100] [NO] |
| R2 VOLUME | [125] [100] [NO] |
| WAVE LENGTH | [545] [570] |
| CALIB. METHOD | [LINEAR] [0] [0] |
| STD (1) CONC. -POS. | [0]-[1] |
| STD (2) CONC. -POS. | [1.0]-[2] |
| STD (3) CONC. -POS. | [0]-[0] |
| STD (4) CONC. -POS. | [0]-[0] |
| STD (5) CONC. -POS. | [0]-[0] |
| STD (6) CONC. -POS. | [0]-[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0.20]-[1.0] |
| TECH. LIMIT | [0]-[100] |
| INSTRUMENT FACTOR | [1.0] |

For the automated urinalysis of urobilinogen, the two part reagent's part one (R1), contains ethylenediaminetetraacetic acid (EDTA sodium salt) to chelate interfering compounds and to activate urobilinogen by adjusting it to an alkaline pH, and sodium lauryl sulfate to act as a surfactant and activator. The second part of the reagent (R2) contains an indicator, 2-methoxy-4-nitrobenzene diazonium tetrafluroborate, lauryl pyridium chloride to eliminate interference from gross amounts of bilirubin, and metaphosphoric acid to adjust pH of the reaction. The reagents are placed in the autoanalyzer. The urine samples, standards, and controls are placed in the autoanalyzer specimen cups. The urine samples, standards and controls are mixed with part one of the reagent (R1) in separate cuvettes. Then the second part of the reagent (R2) is added to the solutions in each cuvette, mixed and this reaction mixture is read at specified intervals as dictated by the instrument parameters and at the specified wavelength (monochromatically) depending on the reagent composition used. In this instance, the assay is read at 545 nanometers and read times are specific to the analyzer. The limit of sensitivity is about 0.00 to 10.00 mg/dl.

It can be noted that no prior art (patent) has cited, taught, or envisioned the use of 2-methoxy-4 nitrobenzene diazonium tetrafuorborate as a substrate for the use of analyzing urobilinogen in urine on an automated analyzer or the unique formulation of EXAMPLE IV. This substrate has the characteristic of long term stability, superior sensitivity and resistance to urinary constituent interference that is a marked advancement in the art of urobilinogen analysis. This art also includes this additional disclosure: Some diazonium salts react with urobilinogen to form red to purple colored complexes only when activated by a base (in this case EDTA trisodium acts as a base as well as a chelator of interfering substances). In addition the presence of sodium lauryl sulfate acts to accelerate the reaction and functions as a surfactant, and inclusion of dodecylpyridium will prevent cross reaction of gross amounts of bilirubin.

EXAMPLE V

Liquid reagents are successfully compounded by dissolving the following chemicals at room temperature (25 degree C.):

| Solution I (R1): | |
| --- | --- |
| sodium hydroxide | 0.1 g |
| EDTA | 1.0 g |
| distilled water add to | 100.0 ml |
| Solution II (R2): | |
| metaphosphoric acid | 2.5 g |
| dodecylbenzenesulfonic acid | 0.1 g |
| 4-methyl-2-nitrobenzene diazonium 1,5-naphthalene disulfonate | 1.0 g |
| isoprpanol | 5.0 ml |
| distilled water add to | 100.0 ml |

| Instrument parameters (Hitachi 717): | |
| --- | --- |
| CHEMISTRY PARAMETERS | |
| TEST | [URINE UROBIL] |
| ASSAY CODE | [1 POINT]:[0]–[50] |
| SAMPLE VOLUME | [10] |
| R1 VOLUME | [125] [100] [NO] |
| R2 VOLUME | [125] [100] [NO] |
| WAVE LENGTH | [545] [570] |
| CALIB. METHOD | [LINEAR] [0] [0] |
| STD (1) CONC. -POS. | [0]–[1] |
| STD (2) CONC. -POS. | [1.0]–[2] |
| STD (3) CONC. -POS. | [0]–[0] |
| STD (4) CONC. -POS. | [0]–[0] |
| STD (5) CONC. -POS. | [0]–[0] |
| STD (6) CONC. -POS. | [0]–[0] |
| SD LIMIT | [999] |
| DUPLICATE LIMIT | [32000] |
| SENSITIVITY LIMIT | [0] |
| ABS. LIMIT (INC/DEC) | [32000] [INCREASE] |
| PROZONE LIMIT | [0] [UPPER] |
| EXPECTED VALUE | [0.20]–[1.0] |
| TECH. LIMIT | [0]–[100] |
| INSTRUMENT FACTOR | [1.0] |

For the automated urinalysis of urobilinogen, the two part reagent's part one (R1), contains ethylenediaminetetraacetic acid (EDTA sodium salt) to chelate interfering compounds and together with sodium hydroxide activates urobilinogen by adjusting it to an alkaline pH. The second part of the reagent (R2) contains an indicator, 4-methyl-2-nitrobenzene diazonium 1,5 naphthalene disulfonate, metaphosphoric acid to adjust pH of the reaction, dodecylbenzene-sulfonic acid to promote reaction between the diazo indicator and urobilinogen and act as a surfactant, and isopropanol to aid in solubilization of the R2 components. The reagents are placed in the autoanalyzer. The urine samples, standards, and controls are placed in the autoanalyzer specimen cups. The urine samples, standards and controls are mixed with part one of the reagent (R1) in separate cuvettes. Then the second part of the reagent (R2) is added to the solutions in each cuvette, mixed and this reaction mixture is read at specified intervals as dictated by the instrument parameters and at the specified wavelength (monochromatically) depending on the reagent composition used. In this instance, the assay is read at 570 nanometers and read times are specific to the analyzer. The limit of sensitivity is about 0.00 to 10.00 mg/dl.

It can be noted that no prior art (patent) has cited, taught, or envisioned the use of 4-methyl-2 nitrobenzene diazonium 1,5 naphthalene disulfonate as a substrate for the use of analyzing urobilinogen in urine on an automated analyzer or the unique formulation of EXAMPLE V. This substrate has the characteristic of long term stability, superior sensitivity and resistance to urinary matrix interference that is a marked advancement in the art of urobilinogen analysis.

The following is an example of a method for analyzing urine, standards or controls for urobilinogen on an automated instrument. First, place an aliquot of the urine, control, or standard to be tested in an automated analyzer sampling cup. Then place the cup in a sampling tray within the automated analyzer, said analyzer transfers the sample to a cuvette mounted within the analyzer, injecting one or more reagent compositions in an aqueous medium into the cuvette, the reagent composition containing one or more chelators or compounds to remove substances in the sample that cause interference in particular with the detection of urobilinogen or in general with any type of colorimetric photometry or the preferred diazo coupling reaction between urobilinogen and the diazo compound, and act as a base which helps to activate urobilinogen, said constituents comprise R-1, and combined with sample first, and followed by the addition of R-2 consisting of a buffer to adjust the pH of the urine to a preferred value, an activating compound that aids in the coupling reaction between urobilinogen and diazo-compound, a surfactant to decrease surface tension and promote mixing on a molecular level and activate the diazo reaction, and color developer consisting of a diazonium salt or salts capable of coupling with urobilinogen or a urobilinogen indicator compound capable of giving a detectable response in the presence of urobilinogen, an amount of acid sufficient for the coupling reaction, and a stabilizing agent to prevent color development and stabilize the diazonium salts without the presence of urobilinogen in a specimen in accordance with a preprogrammed code introduced into the automated analyzer (see instrument Parameters in EXAMPLES I–V), at a preprogrammed monochromatically specified wavelength to compare absorbance of the patient's urine, or other fluid, and reagent composition complex with a standard containing a known concentration of urobilinogen and thereby determining the presence or absence of urobilinogen in the sample.

This device (method) can use a one-part reagent (see EXAMPLES I and III) or two-part reagent (see EXAMPLES II, IV and V) composition in an aqueous medium injected into the cuvette.

This device's (method's) reagent compositions can contain compounds that include chelators or other compounds to remove substances in the urine that causes interference with colorimetric photometry or the preferred reaction between urobilinogen and the color developer, and act as a base which helps to activate urobilinogen, said constituents comprise R-1, and combined with sample first, and followed by the addition of R-2 consisting of other compounds including 2-methoxy-4-nitrobenzene diazonium tetrafluoroborate, 4-methyl-2-nitrobenzene diazonium 1,5 naphthalene disulfonate, or 4 methoxybenzene diazonium tetrafluroborohydrate which act as the color indicator specific for urobilinogen, dodecylbenzenesulfonic acid or sodium lauryl sulfate, which act as activators and surfactants, metaphosphoric acid which adjusts reagent/sample complex to an acidic pH to stabilize the indicator salt and promote formation of the urobilinogen reaction with the diazo compound, and dodecylpyridium chloride to inhibit interference of bilirubin with the reaction, and a short chain alcohol to aid in solubilization of these components all of which comprise the R-2 reagent; and when combined with a urobilinogen-containing specimen and R1 form a colored complex measurable by the autoanalyzer's spectrophotometer.

This device's (method's) reagent compositions can contain compounds to neutralize urine matrix interference and increase urine sample/reagent compatibility with an automated analyzer, a compound to buffer pH of the urine, control, or standard, to a acidic value, one or more compounds to remove substances in the specimens, that may cause interference with colorimetric photometry, an activating compound that aids in the diazo coupling reaction between urobilinogen and diazonium salts, a surfactant to decrease surface tension and promote mixing on a molecular level and activate the diazo coupling reaction, and a diazonium salt or salts capable of coupling with urobilinogen or an indicator capable of giving a detectable response in the presence of urobilinogen, an amount of an acid sufficient for the diazo coupling reaction, and a stabilizing agent to prevent color development and stabilize the diazonium salts without the presence of urobilinogen.

This device's (method's) wavelength of the analyzer can vary from about 340 to 700 nanometers. And finally, this device comprises contacting a test sample with a reagents composition to detect urobilinogen as illustrated in EXAMPLES I through V.

It will be understood that the specification and examples are meant to illustrative, but not limit the present invention and that other embodiments within the spirit and scope of the invention will suggest themselves to those skilled in the art.

What is claimed is:

1. A method for detecting urobilinogen in a patient's urine comprising the steps of:

A.) placing aliquots of a patient's urine and a standard to be tested in automated analyzer sampling cups, B.) placing the cups in a sampling tray within an automated analyzer, transferring the aliquots of urine and standard to cuvettes mounted within the automated analyzer, injecting a first and a second reagent composition in an aqueous medium into the cuvettes, the first reagent composition containing chelators or other compounds that remove substances in urine that cause interference with colorimetric photometry and that act as a base which helps to activate urobilinogen, wherein said first reagent composition comprises R1 which is combined with the aliquots of urine and standard first, and is followed by the addition of a second reagent composition, wherein said second reagent composition comprises R2 and contains a buffer to adjust the pH of the urine to an acidic value, an activating compound, a surfactant to decrease surface tension and promote mixing on a molecular level, a color developer consisting of an indicator salt capable of a coupling reaction with urobilinogen or compounds that will give a detectable response in the presence of urobilinogen, an amount of an acid sufficient for the reaction of urobilinogen with the color developer, and a stabilizing agent to prevent color development and stabilize the indicator salt without the presence of urobilinogen in urine, and C.) reading absorbance values for the aliquots of urine and standard at specified intervals, in accordance with a preprogrammed code introduced into the automated analyzer, at a preprogrammed monochromatically specified wavelength, to compare absorbance of the first and second reagent composition plus the patient's urine with that of the first and second reagent composition plus the standard containing a known reference concentration of urobilinogen and thereby determining the presence or absence of urobilinogen in the patient's urine.

2. The method according to claim 1 wherein the first and second reagent compositions are first combined together and then injected into the cuvettes as a single reagent composition.

3. The method according to claim 2 wherein the single reagent composition contains compounds to neutralize urine matrix interference and increase urine sample reagent compatibility with the automated analyzer, a compound to buffer the pH to an acidic value, one or more compounds to remove substances in urine that cause interference with the detection of urobilinogen or general interferants in any type of colorimetric photometry, an activating compound that aids in the reaction between urobilinogen and the color developer, a surfactant to decrease surface tension and promote mixing on a molecular level, an indicator capable of coupling with urobilinogen, an acid, and a stabilizing agent to prevent color development and stabilize the indicator without the presence of urobilinogen in urine.

4. The method according to claim 1 wherein the wavelength of the automated analyzer is about 340 to 700 nanometers.

5. Method for detecting urobilinogen in body fluids comprising the steps of:

A.) contacting a test sample comprised of urine suspected of containing urobilinogen or a standard with a first reagent composition comprised of chelators or other compounds that remove substances in urine which cause interference with colorimetric photometry and that act as a base which helps to activate urobilinogen, wherein said first reagent composition comprises R1 which is combined with the test sample of urine or standard first, and followed by the addition of a second reagent composition comprising R2 that includes a diazo-containing compound selected from the group consisting of 2-methoxy-4-nitribenzene diazonium tetrafluoroborate, 4-methyl-2-nitrobenzene diazonium-1,5-naphthalene disulfonate and 4-methoxybenzenediazonium tetrafluoroborate which acts as a diazo color developer specific for urobilinogen, dodecylbenzene-sulfonic acid which acts as an activator and surfactant, and metaphosphoric acid which adjusts the pH to an acidic value and stabilizes a reaction between urobilinogen and the diazo-containing compound, and B.) placing the combination of the first reagent composition R1, the second reagent composition R2 and the test sample of urine or standard into an automated analyzer to read absorbance values in accordance with a preprogrammed code introduced into the automated analyzer, at a preprogrammed monochromatically specified wavelength, wherein the combination of said first reagent composition R1, said second reagent composition R2 and the test sample of urine or standard reacts to form a diazo/urobilinogen colored complex detectable by the absorbance values if urobilinogen is present in the test sample of urine or standard.

6. The method according to claim 5 wherein the second reagent composition R2 further includes lauryl pyridinium chloride or dodecyl pyridinium chloride to inhibit bilirubin interference with the diazo/urobilinogen colored complex.

* * * * *